United States Patent [19]

Loosen et al.

[11] Patent Number: 5,356,637
[45] Date of Patent: Oct. 18, 1994

[54] METHOD FOR PREPARING AN ENZYMATIC HYDROLYSATE

[75] Inventors: Pierre C. Loosen, Tessenderlo, Belgium; Philippe R. Bressollier, Limoges, France; Raymond A. Julien, Limoges, France; Claude H. Pejoan, S.-Sylvestre, France; Bernard G. Verneuil, Verneuil-sur-Vienne, France

[73] Assignee: Tessenderlo Chemie N.V., Tessenderlo, Belgium

[21] Appl. No.: 927,639

[22] PCT Filed: Sep. 11, 1991

[86] PCT No.: PCT/BE91/00001

§ 371 Date: Sep. 4, 1992

§ 102(e) Date: Sep. 4, 1992

[87] PCT Pub. No.: WO91/10369

PCT Pub. Date: Jul. 25, 1991

[30] Foreign Application Priority Data

Jan. 12, 1990 [BE] Belgium .................. 9000044

[51] Int. Cl.$^5$ .................. A23L 1/00
[52] U.S. Cl. .................. 426/7; 426/18; 426/32; 426/34; 426/44; 426/49; 426/656; 426/657; 435/68.1; 435/212
[58] Field of Search .................. 426/7, 41, 49, 52, 656, 426/18, 32, 34, 42, 44, 46, 47, 49, 55, 56, 63, 657; 435/68.1, 212, 213, 214, 215, 216, 217, 218, 219

[56] References Cited

U.S. PATENT DOCUMENTS

| | | | |
|---|---|---|---|
| 3,857,966 | 12/1974 | Feldman et al. | 426/7 |
| 4,107,334 | 8/1978 | Jolly | 426/7 |
| 4,145,455 | 3/1979 | Fujimaki et al. | 426/656 |
| 4,293,571 | 10/1981 | Olofsson et al. | 426/7 |
| 4,294,856 | 10/1981 | Kinumaki et al. | 426/7 |
| 4,361,586 | 11/1982 | Meinke | 426/7 |
| 4,427,658 | 1/1984 | Maubois et al. | 426/42 |
| 4,579,660 | 4/1986 | Toushek et al. | 426/657 |
| 4,627,983 | 12/1986 | Scharf et al. | 426/7 |
| 4,940,662 | 7/1990 | Yamazaki et al. | 426/46 |

FOREIGN PATENT DOCUMENTS

| | | |
|---|---|---|
| 0044032 | 1/1982 | European Pat. Off. |
| 0065663 | 12/1982 | European Pat. Off. |
| 0148072 | 7/1985 | European Pat. Off. |
| 0274939 | 7/1988 | European Pat. Off. |
| 0274946 | 7/1988 | European Pat. Off. |
| 2367773 | 5/1978 | France |

Primary Examiner—Donald E. Czaja
Assistant Examiner—Leslie Wong
Attorney, Agent, or Firm—Sughrue, Mion, Zinn, Macpeak & Seas

[57] ABSTRACT

An enzymatic hydrolysate having a high di- and tripeptide content is prepared by subjecting to enzymatic proteolysis a protein mixture preliminarily prepared by means of a thermal treatment. The hydrolysate having a high di- and tripeptide content is extracted by liquid-solid separation, followed by ultrafiltration. The hydrolysate is then subjected to a sterilization and drying operation.

14 Claims, No Drawings

METHOD FOR PREPARING AN ENZYMATIC HYDROLYSATE

BACKGROUND OF THE INVENTION

The invention relates to a method for preparing an enzymatic hydrolysate containing di- and tripeptides, from a protein mixture, using proteolytic enzymes.

The subject of the present invention is also a di- and tripeptide-rich hydrolysate.

The importance of hydrolysates rich in di- and tripeptides and having a low free amino acid content is widely recognised by numerous scientific studies.

The physiological importance of the intestinal absorption of di- and tripeptides was discovered about thirteen years ago. Thus, the existence of intestinal transport systems for small peptides, different from those for free amino acids, and the greater efficacy of the absorption when the food supply of proteins is achieved from mixtures enriched with small peptides, have been demonstrated by SLEISENGER et al. in an article entitled "Evidence for a single common carrier for uptake of a dipeptide and tripeptide by hamster jejunum in vitro" published in the journal "Gastroenterology", volume 71, pages 76 to 81 (1976).

Compositions rich in di- and tripeptides are of real interest in dietetics not only for the nutrition of infants, convalescents and anaemic individuals, but also for that of patients whose intestinal absorption is altered, such as patients suffering from HARTNUP disease or cystinuria.

Both in individuals suffering from HARTNUP disease and in those suffering from cystinuria, amino acids are normally absorbed by the intestinal mucosa if they are present in dipeptide form (see BRINSON, R. R., HANUMANTHU, S. K., and PITTS, W. M. (1989): "A reappraisal of the peptide based enteral formulas: clinical applications", Nutritional in Clinical Practice 4:211–217; NAYAB, F. and ASATOOR, A. M. (1970): "Studies on intestinal absorption of amino acids and a dipeptide in a case of Hartnup disease", Gut (Journal of the British Society for Gastroentology) volume 11, pages 373–379 (1970)).

Consequently, the invention can for example be applied in hospital diets, in particular in artificial nutrition administered orally, enterally or parenterally, more particularly by intravenous infusion.

Artificial nutrition is essential for patients incapable of normal feeding because of an incapacity due to a physical damage caused by an accident, a surgical operation, an oesophageal trauma or because of a general physiological state which does not permit normal feeding, (coma, burns).

Other possible applications are immunostimulation or animal nutrition, particularly fish feed, or use as growth stimulator.

Various methods are known for preparing protein hydrolysates containing di- and tripeptides: alkaline or acid hydrolysis, enzymatic hydrolysis and chemical synthesis. However, all of these known methods do not enable a hydrolysate containing not less than 75 mole % di- and tripeptides to be prepared from animal and/or vegetable proteins.

Proteins which can be used for manufacturing a hydrolysate on an industrial scale are, by way of example, as follows:

egg proteins (ovalbumin);

milk proteins: casein, whey, lactalbumins, lactoglobulins;

slaughtering blood proteins: blood plasma, serum albumin, decolorised haemoglobin;

products from the fishing and fish-canning industries, and proteins of plant origin: soybean and lucerne proteins.

Alkaline hydrolysis or acid hydrolysis of mixtures of proteins such as lactalbumin, ovalbumin, whey and casein by means of strong acids or bases is used at high temperature so as to break the chemical bonds. It leads to the production of mixtures which are greatly enriched in free amino acids and often very highly contaminated with salts ($Cl^-$, $Na^+$) which are difficult to remove.

The known chemical methods are easy to implement and enable high levels of hydrolysis to be obtained by breaking a large number of peptide bonds. However, they are drastic and cause the formation of undesirable side reactions as well as a decrease in the nutritional value of the proteins through the degradation of essential amino acids.

Thus, alkaline hydrolysis at high temperature (100° to 110° C.) often generates the formation of lysinoalanine, a very toxic by-product. Moreover, it is difficult to control the degree of hydrolysis of the finished product.

Proteolytic enzymes which may be used for the enzymatic hydrolysis are enzymes of bacterial, fungal, animal and/or plant origin.

The action of one or more of these enzymes on one or more of these proteins leads to hydrolysates containing not more than 50% of di- and tripeptides.

For example, a method for preparing a di- and tripeptide-rich peptide mixture, which may be used in artificial nutrition and in dietetics, by chromatographic extraction of the di- and tripeptides from an enzymatic protein hydrolysate containing 10 to 50% by weight of di- and tripeptides as well as polypeptides which are larger than tripeptides, is known from the document EP-A-0,274,939.

The substrate for the enzymatic hydrolysis consists of one or more animal or vegetable proteins, for example egg, milk, slaughtering blood and/or soybean or lucerne protein. The enzymatic hydrolysate is purified by ultrafiltration. The purified hydrolysate is then loaded onto an ion exchange resin column in order to increase the proportions of di- and tripeptides in the mixture.

In spite of the use of a mixture of enzymes, enzymatic hydrolysate which is not enriched on an exchange resin column contains not more than 50% of di- and tripeptides, not less than 7% of free amino acids as well as an excessively high percentage of ions (see Table 1 on page 8 of the document mentioned).

The hydrolysate is purified on a cation exchange resin column in order to increase the proportions of di- and tripeptides in the mixture and to decrease the salt concentration. This di- and tripeptide enrichment stage has the disadvantage of decreasing the weight yield but also of being troublesome and expensive.

The document EP-A-0,148,072 describes a method for the proteolysis of plasma proteins in order to provide protein hydrolysates suitable for human and animal nutrition by virtue of their acceptable savour and taste. In this method, the blood plasma serving as hydrolysis substrate is obtained by centrifugation of whole blood collected in the presence of an anticoagulant, on slaughtering. A yellow, light phase, the plasma, and a red, heavy phase, the cruor, are obtained by centrifugation in a separator.

Denaturation of the plasma is carried out beforehand by heat treatment of the proteins at a temperature of 70° to 100° C., the pH being maintained at a value of 5 to 7 for less than 30 minutes, so as to increase the proteolysis yield.

Proteolysis of the plasma proteins is then carried out by adding them to an aqueous reaction medium containing thermolysin, in the presence of calcium ions at a pH of 5 to 7 and at a temperature of not more than 80° C.

The proliferation of mesophilic bacteria is avoided by the use of a range of temperatures between 50° and 60° C.

The judicious choice of enzymes and of hydrolysis conditions results in peptides of defined sizes being obtained as required.

The disadvantage of this known method lies, inter alia, in the low weight yield of di- and tripeptides from the proteolysis. Indeed, filtration of the hydrolysate on Biogel P6 reveals the presence of peptides with a molecular mass of less than 2000, that is to say a mixture of free amino acids and peptides containing 2 to 10 amino acids, the di- and tripeptide content remaining very low. In artificial nutrition, however, peptides of more than three amino acids do not provide the kinetic advantages of the absorption described above.

SUMMARY OF THE INVENTION

The subject of the present invention is a method for preparing a di- and tripeptide-rich enzymatic hydrolysate from a protein mixture, in the presence of proteolytic enzymes, in which the starting protein mixture is prepared by heat treatment, the prepared mixture is subjected to enzymatic hydrolysis, the hydrolysate is extracted by liquid/solid separation, and then the partially hydrolysed soluble proteins as well as the peptides with a molecular mass of more than 10,000 are removed therefrom by ultrafiltration, before it is subjected to a sterilising and drying operation.

The method according to the invention has, for example, the advantage of enabling not less than 70% by weight of proteins to be converted to a peptide fraction containing not less than 75 mol % of di- and tripeptides.

The heat treatment of the proteins causes modification of their three-dimensional structure by acting on the weak bonds responsible for the native conformation. It leads to greater exposure of the peptide linkages constituting the primary structure and thus improves the accessibility of the substrate to the enzymes.

According to one feature of the invention, after dissolving a substrate or a mixture of proteins in water, the solution thus obtained is subjected to heat treatment at a temperature of between 70° and 100° C., at atmospheric pressure advantageously for a period of less than 45 minutes at the initial pH or at acidic pH or at close to neutral pH, in order to obtain an aqueous protein suspension which is finally subjected to hydrolysis in the presence of proteolytic enzymes. Advantageously, the substrate or protein mixture is dissolved in water in order to obtain a solution whose substrate or protein concentration is less than 100 g/l, preferably of about 70 g/l (N ×6.25). The heat treatment is preferably carried out for 30 to 45 minutes. The hydrolysis is advantageously carried out at pH values of between 6.5 and 9, preferably 7 and 7.5, and at temperatures of between 50° and 60° C. for 5 to 9 hours.

Although the hydrolysis can be carried out at a pH value of between 6.5 and 7, it is preferably carried out at pH values of between ? and 9.

The method according to the invention can be applied to various protein sources such as:

slaughtering blood proteins;

milk proteins: caseinate, whey, α-lactalbumin, β-lactoglobulin;

soybean, pea and/or wheat proteins, fish isolates, egg white proteins and the like.

DESCRIPTION OF PREFERRED EMBODIMENTS

In a particular embodiment of a method according to the invention, animal blood is collected by adding less than 4 g/l of anticoagulant and is subjected to centrifugation in order to obtain a product which can be used immediately or which is suitable for preservation by freezing or drying by spray-drying, and then after adjusting to acidic pH such as a pH of 4.5 to 5, the blood plasma thus obtained is subjected to a heat treatment in a temperature range between 70° and 80° C. for a period of less than 45 minutes, preferably of between 30 and 45 minutes, and then to liquid/solid separation by tangential microfiltration, centrifugation, or by filtration under pressure or vacuum (preferably on a filter press), in order to obtain a heat-coagulated solid substrate which is finally subjected to hydrolysis in the presence of proteolytic enzymes after resuspension.

For the hydrolysis, the enzyme used is advantageously a protease which can be used in an alkaline medium and is, preferably, a serine-containing alkaline protease, in particular a *Bacillus licheniformis subtilisin* (Pescalase ®- Gist Brocades; Alcalase ®- NOVO), a *Bacillus subtilis subtilisin* (Orientase 100 ®- HANKYU, Japan), a *Bacillus amyloquefaciens subtilisin* (subtilisin BP N'; Carlsberg Res. Commun., vol. 41, no. 5, pages 238 to 241, 1976, I. B. SVENDSEN).

Using the method according to the invention, it has been possible to prepare a di- and tripeptide-rich hydrolysate which is provided in the form of a pulverulent mass, preferably white, of mild savour and pleasant taste, containing:

not less than 75 mol % of di- and tripeptides;

less than 5 mol % of amino acids;

less than 20 mol % of peptides of more than three amino acids, the mean chain length being equal to about 6.2. It has never been possible to prepare such hydrolysates by mere hydrolysis using animal and/or vegetable proteins as starting material.

Features and details of the invention relative to the various substrates are presented below by way of non-limitative examples.

The following experiments are performed on a pilot scale in an equipment (of 20 to 300 liters of reaction medium) foreshadowing the industrial scale. The protein sources used are prepared as indicated below.

I. ANIMAL BLOOD PLASMA

Blood consists of a liquid called plasma, in which organised elements consisting of erythrocytes or red blood cells, leucocytes or white blood cells and blood platelets, are suspended. After adding an anticoagulant, centrifugation enables, on the one hand, the plasma (60 to 65% by vol.), and on the other hand, the organised elements which constitute the cruor (35 to 40% by vol.), to be recovered.

The method for preparing a composition according to the invention from slaughtering blood comprises the following four essential stages:

1. conditioning of the animal blood plasma;
2. enzymatic hydrolysis;
3. extraction and purification of a di- and tripeptide-rich fraction; and
4. sterilisation and drying of the di- and tripeptide-rich fraction.

1. - CONDITIONING OF THE ANIMAL BLOOD PLASMA

The whole blood from slaughtering is collected at the slaughterhouse in the presence of anticoagulant. To this effect, not more than 4 g/l of potassium or sodium oxalate, citrate or polyphosphate is added. This blood is then subjected to centrifugation.

The plasma thus collected is either used immediately as it is, or immediately frozen or dried for its preservation for subsequent use.

After redissolving at a concentration of about 70 g/l (N ×6.25), the frozen or spray-dried plasma is adjusted to a pH of less than 6 and heated to a temperature above 65° C. The conditions leading to a maximum precipitation of the plasma proteins are selected.

Preferably, the pH of the animal plasma is reduced to between 4.5 and 5.0 using a strong food acid (HCl, $H_2SO_4$ or preferably 4 to 6 normal $H_3PO_4$), while the temperature of the protein solution is increased to 70° C. in a time interval of less than about 30 minutes, this temperature is maintained for 30 minutes and then it is rapidly decreased (5 to 10 minutes) to about 20° C. 95% by weight of protein nitrogen is then recovered in the form of a coagulate whose mean protein content is 160 to 220 g $kg^{-1}$.

Phosphoric acid is generally used during the reduction of the pH of the animal plasma because the phosphate ions have the property of forming insoluble precipitates with divalent cations, especially those subsequently provided by the $Ca(OH)_2$ alkalis used during the enzymatic hydrolysis, for example. Thus, it is possible to significantly reduce the level of calcium in the finished product by the use of phosphoric acid during the preliminary substrate conditioning stage.

After heat treatment, the blood plasma is subjected to a liquid/solid separation.

The liquid/solid separation is carried out by tangential microfiltration, centrifugation or filter press filtration. Currently, plate and frame filter press filtration gives the best results.

This heat treatment, followed by liquid/solid separation, has the following advantages:
- it increases the accessibility of the substrate to the enzyme;
- it destroys most of the protease inhibitors;
- it significantly decreases the contaminant mesophilic flora;
- it removes free amino acids and other small molecules of nonprotein nature (lipids, sugars, urea and the like); and
- it decreases the ionic strength of the protein substrate solution after removal of the ions during the liquid/solid separation by filtration or centrifugation.

The partially desalted protein coagulate is used immediately in an enzyme reactor or alternatively preserved in a freezer at −20° C.

2. - ENZYMATIC HYDROLYSIS

A. Choice of enzyme (protease)

The hydrolysis reaction is optimal for any protease which makes it possible to obtain a plasma protein solubilisation level of more than 90% in acidic medium (ratio of acid-soluble proteins in trichloroacetic acid at 100 g $l^{-1}$ to total proteins subjected to the hydrolysis) as well as a molar concentration of di- and tripeptides representing not less than 75 mol % of the di- and tripeptide-enriched fraction.

The most suitable proteases are of the alkaline, serine protease type such as those derived from *Bacillus licheniformis* whose major component is subtilisin from Carlsberg (EC 3.4.4.16).

By way of example, Alcalase 2, 4 1 (NOVO) or Pescalase 560 (GIST BROCADES) type industrial proteolytic enzymes may be chosen.

For pH values of between 7 and 9, preferably between 7.0 and 7.5, the bovine plasma-hydrolysing reaction by Alcalase ® (NOVO) or by Pescalase ® (GIST BROCADES) is optimal. Furthermore, at these pH values which are relatively close to neutral pH, the amounts of alkalis required to maintain the pH during proteolysis, are substantially smaller than at alkaline pH values (8 to 9). This observation should not be overlooked insofar as the removal of ions, at the end of the manufacturing process, is difficult.

During the hydrolysis reaction, the alkalis used for maintaining the pH may be very wide-ranging (KOH, $Ca(OH)_2$, NaOH, and the like). In order to limit the ionic strength in the product resulting from the hydrolysis, lime ($Ca(OH)_2$) will be generally chosen as alkali for controlling and maintaining the pH.

The most appropriate reaction temperatures are between 50° and 60° C., so that the proteolysis proceeds rapidly and the denaturation of the enzyme is minimal.

However, the choice of a temperature equal to 60° C. makes it possible to decrease the reaction time (5 hours instead of 9 hours at 50° C.) and to limit, more significantly, bacterial proliferation during a the hydrolysis.

The combination of a neutral or substantially neutral pH (7 to 7.5) and a temperature of between 50° and 60° C., makes it possible to obtain a plasma protein solubilisation level, in acidic medium, above 90% and a di- and tripeptide level of not less than 75%, in the case of reaction times ranging from 5 h to 9 h, this being when the proteases used are either Alcalase ® (NOVO), or Pescalase ® (GIST BROCADES).

The weight ratio is defined by the following equation:

$$\frac{\text{Enzyme mass}}{\text{Protein substrate mass}} \times 100 = \frac{E}{S} \text{ in \%}$$

in which the enzyme mass is equal to the mass of industrial preparation of Alcalase or Pescalase introduced into the reaction medium. The substrate mass is equivalent to the mass of plasma proteins introduced into the reactor. It is measured by the Kjeldahl method (amount of elemental nitrogen ×6.25).

The weight ratio of the respective enzyme and protein substrate concentrations should be between 1 and 4% which corresponds to 24 to 96 International Units (I.U.) per gram of substrate of 0.024 or 0.096 Anson-unit per gram of substrate.

Moreover, the protein substrate concentration in the reactor should be the highest possible, while permitting good homogeneity of the medium.

By way of example, an E/S ratio of 2% and a substrate concentration of about 90 g $l^{-1}$ appears to be optimal.

B. Destruction of the enzyme.

When the proteolysis reaction is considered to be complete, destruction of the enzyme is carried out by reducing the pH to between 5.5 and 6.5, by adding a strong, food acid (HCl, $H_2SO_4$, $H_3PO_4$ and the like), preferably $H_3PO_4$.

The combination of a reduction of the pH of the medium with an increase of the temperature is the best compromise.

The temperature is rapidly increased (in 10 to 20 minutes) up to a value of between 70° and 80° C. and then this temperature is maintained for 5 to 45 minutes. After this heat treatment, the temperature of the medium is rapidly decreased to a value of between 15° and 20° C.

The pH is preferably reduced to 6.5 and the temperature is maintained at 80° C. for 20 minutes. The special operating conditions permit complete destruction of the protease without any trace of activity being detectable by reference tests, while avoiding the generation of toxic derivatives such as lysinoalanine.

3. - PURIFICATION OF THE DI- AND TRIPEPTIDE-ENRICHED HYDROLYSATE a. Clarification After enzymatic hydrolysis of the animal plasma, the reaction medium is subjected to clarification either by centrifugation or by filtration (tangential microfiltration, filter press filtration and the like) in order to remove insoluble protein residue, residual plasma lipids as well as inorganic precipitates such as calcium phosphates.

For example, a plate and frame filter press is used in the presence of a diatomite type filter aid (Spendalite N) at a concentration of 30 to 50 g.$kg^{-1}$.

b. Ultrafiltration

The filtration-clarified hydrolysate is subjected to an ultrafiltration stage on organic type membranes (potysulphone) packaged as hollow fibre modules (Amicon), as flat modules (Millipore) or as spiral modules (Millipore-Amicon) or alternatively on inorganic type (ceramic) membranes packaged as multichannel modules (Tech Sep). The partially hydrolysed soluble proteins as well as the peptides with a molecular mass above 10,000, are removed by ultrafiltration before subjecting the hydrolysate to a sterilising and drying operation. The peptide fraction recovered in the ultrafiltrate constitutes the di- and tripeptide-rich composition. The molecular weight cut-off of the membranes should be between 1,000 and 10,000.

4. - DEGERMINATING FILTRATION AND DRYING OF THE DI- AND TRIPEPTIDE-RICH COMPOSITION (DTP)

The di- and tripeptide-rich mixture resulting from the ultrafiltration is subjected, within the shortest possible delay (not exceeding 24 h of preservation in a refrigerator at +4° C.), to degerminating filtration intended to remove all the bacterial contaminants still present in the mixture.

To this effect, Millipore, Sartorius type filtration systems and the like may be used.

The filtrability of the product being very good, the filtration system to be used is simple:

a 2 to 0.65-micron prefilter;

a 0.22-micron absolute filter.

The product thus filtered is collected in a sterile receptacle before being subjected to dehydration. The removal of water may be achieved either by freeze-drying or by spray-drying coupled or not with a preconcentration by evaporation under vacuum.

The separation and quantification of the peptides on the basis of the number of their constituent amino acid residues, which is undoubtedly a difficult problem to solve, was solved by using a recent high performance ligand-exchange chromatography technique (HPLEC).

Gel permeation chromatography is a recent specific technique. However, it does not separate the small peptides on the single criterion of their mass because there is overlapping of the elution zones of di- and tripeptides of varying masses; this is linked in particular to the existence of multiple peptide/gel interactions. Furthermore, because of the overlappings of the mass domains of families of varying sizes, the distribution of molecular masses does not enable a complex mixture of small peptides to be characterised on the basis of their size criterion. For all these reasons, the quantification of di- and tripeptides is generally not accurately performed.

By developing a high performance ligand-exchange chromatography technique (HPLEC) on copper-coated silica coupled with Edman chemical degradation, it was possible to carry out a direct assay of the amino acids and nonbasic dipeptides and an indirect assay of the tripeptides. The quantification of the amino acids of nonbasic dipeptides and larger-sized peptides is carried out by fluorescence spectrometry after reduction to the amino acid form.

The hydrolysate obtained by this method according to the invention is in the form of a white pulverulent mass of mild savour and pleasant taste, which has the following composition:

not less than 40 mol % of di and 35 mol % of tripeptides;

less than 5 mol % of amino acids; and less than 20 mol % of oligopeptides above three amino acids, the mean chain length being equal to about 6.2;

osmolality of 250 milliosmoles/liter at a concentration of 11.2 g of free nitrogen per liter.

The dry matter of the powder obtained at the end of the treatment is 94–96%.

In the next paragraph, a method according to the invention was applied to whey as well as to various protein isolates.

II. WHEY, FISH ISOLATE, PEA ISOLATE, SOYBEAN ISOLATE AND WHEAT ISOLATE

Various substrates were treated in a method according to the invention. These substrates were, inter alia:

milk serum or whey, that is to say a by-product of the cheese industry obtained during the liquid/solid separation of chemically or biologically insolubilised casein;

a fish protein concentrate provided in the form of a light beige powder, not very hygroscopic, containing 72 to 74% by weight of proteins, 3 to 6% fat, 12 to 15% inorganic matter and 3 to 5% residual humidity;

a pea isolate consisting of natural vegetable extracts produced from selected and shelled pea grains;

a wheat isolate provided in the form of a white or beige powder, neutral in taste, containing about 86% by weight of proteins; and a soybean isolate containing more than 90% by weight of proteins.

Industrially, the soybean proteins are preferably solubilised and then separated from the insoluble coproducts. The efficiency of the liquid/solid separation between the protein solution and the insoluble coproducts determines the degree of purification of the isolate prepared. The proteins are, in a second stage, selectively recovered by purification at the isoelectric point.

The degree of purification of the soybean protein isolates (and conversely the low salt, lipid and fibre contents) makes it possible to avoid carrying out an additional purification stage.

1. CONDITIONING OF THE SUBSTRATES

The heat treatment conditions for each of the substrates were as follows:

A milk serum protein concentrate, fish isolate, pea isolate, soybean isolate and/or wheat isolate was acidified to pH 4.6 by a strong food acid (HCl, $H_2SO_4$ or preferably 4 to 6 normal $H_3PO_4$) and then heated to 85°-100° C. in less than about 30 minutes and maintained at this temperature for a period of less than 45 minutes, namely 30 minutes. The temperature is then rapidly reduced (5 to 10 minutes) to about 60° C. A high degree of purification of the substrate and conversely a low ash content made it possible to eliminate the post-heat-treatment liquid/solid separation stage.

2. ENZYMATIC HYDROLYSIS

The enzymatic hydrolysis conditions were:
a neutral alkaline pH of 7 to 9;
a temperature of 30° to 70° C., preferably 50° to 60° C.;
a duration preferably ranging between 5 and 9 hours.

The enzymatic hydrolysis stage was stopped by destroying the enzymatic activity, for example by reducing the pH to 5.5 to 6.5 by the addition of a strong food acid and heating at 75°-80° C. for 5 to 30 minutes.

The method then comprised, in a manner similar to the plasma treatment method, clarification, ultrafiltration, degerminating filtration and drying.

The compositions of the substrates, the nitrogen yields of the clarification and ultrafiltration stages and the compositions of the hydrolysates obtained are collated in Tables 1 to 3 respectively.

TABLE 1

| COMPOSITION OF THE SUBSTRATE BEFORE HEAT TREATMENT AND HYDROLYSIS (% by weight) | | | | | | |
|---|---|---|---|---|---|---|
| RAW MATERIAL | SUPPLIER | $H_2O$ % | Proteins % | Ash % | Fat % | Others % |
| 1. Blood plasma | NORDFLEISCH (D) | 5–7 | 75 | 6 | | |
| 2. Bovine milk serum PROTARMOR 90 | ARMOR PROTEINE (F) | 5 | 90 | 3 | 1.5 | 1* |
| 3. Fish isolate CORPESCA | SOPROPECHE (F) | 10 | 66 | 16 | 9 | |
| 4. Soybean isolate ARDEX SP 6 | ARKADY ADM (F) | 6 | 91.5 | 4.5 | 0.5 | |
| 5. Pea isolate | COSUCRA (B) | 6 | 88 | 5 | 0.2 | |
| 6. Wheat isolate AMYPRO SWP | AMYLUM (B) | 5 | 86 | 5 | 8 | 1 |
| 7. Ca caseinate | ARMOR PROTEINE (F) | 6 | 88 | 4.5 | 1.5 | 0.2 |
| 8. Egg white protein | IGRECA (F) | 8 | 78 | 6 | 0.5 | 0.7 |

*% lactose

TABLE 2

| YIELDS OF THE CLARIFICATION AND ULTRAFILTRATION STAGES | | |
|---|---|---|
| Raw material | Nitrogen yield after clarification | Nitrogen yield after ultrafiltration |
| 1. Blood plasma | 80% | 70% |
| 2. Bovine milk serum | 80% | 70% |
| 3. Fish isolate | 86% | |
| 4. Soybean isolate | 73% | 65% |
| 5. Pea isolate | 76% | 69% |
| 6. Wheat isolate | 76% | |
| 7. Ca caseinate | 78% | 68% |
| 8. Egg white proteins | 62% | 58% |

TABLE 3

| AMINO ACID AND PEPTIDE COMPOSITION OF THE HYDROLYSATE | | | | |
|---|---|---|---|---|
| | RELATIVE CONTENT IN MOL % | | | |
| RAW MATERIAL | Free amino acids | Dipeptides | Tripeptides | Oligopeptides larger than the tripeptides |
| 1. Bovine plasma | <5 | >40 | >35 | <20 |
| 2. Bovine milk serum | <5 | >40 | 30–40 | 15–25 |
| 3. Fish isolate | <7 | >37 | 30–40 | 16–26 |
| 4. Soybean isolate | <5 | >43 | 30–35 | 17–22 |
| 5. Pea isolate | <4 | >44 | 30–35 | 17–22 |
| 6. Wheat isolate | <4 | >48 | 30–35 | 13–18 |
| 7. Ca caseinate | <4 | >45 | 30–40 | 11–21 |
| 8. Egg white proteins | <3 | >42 | 30–40 | 15–25 |

III. CALCIUM CASEINATE

The methods currently used for extracting casein from milk are based on the insolubilisation of this protein using a biological or chemical route. A suspension of casein in milk serum is thus obtained which can be easily purified by liquid/solid separation and washing with an aqueous medium.

This preliminary casein purification stage makes it possible to avoid a liquid/solid separation stage after the heat treatment.

Casein is a sparingly soluble protein. The solubilisation of casein is industrially performed at high temperature and at basic pH. Following this denaturing treatment the protein molecules are reduced to the monomeric form, in aqueous solution.

Calcium caseinate is derived from fresh casein resulting from a lactic fermentation.

CONDITIONING

The substrate conditioning conditions are as follows: heating to 90° C.

maintaining at 90° C. for 30 minutes the substrate of a calcium caseinate solution at 77 g/l (N ×6.38) without modification of pH (initial pH 6.8).

In this example, the pH could also have been adjusted to values close to neutral pH (pH 6 to 8).

ENZYMATIC HYDROLYSIS

The temperature is then decreased to 60° C. and the pH of the aqueous solution is adjusted to 7.5 by means of a solution of calcium hydroxide.

The substrate is then subjected to enzymatic hydrolysis, clarification, ultrafiltration and dehydration under the same conditions as those described for the plasma proteins.

Under these operating conditions, the clarification and ultrafiltration rates are normal and are indicative of good proteolytic digestion (Table 2 - line 7).

The results of analysis of the calcium caseinate hydrolysate are collated in Table 3, in line 7.

IV. EGG PROTEINS

Egg white proteins represent a mixture of about twelve distinct proteins, with an isoelectric pH between 4 and 11. Furthermore, some are heat-sensitive and gelling while others are heat-resistant.

CONDITIONING

In order to avoid the disadvantages of the gelling of egg white proteins, the prior heat treatment comprises the following stages:

1) Adjusting a solution of egg white at 85 g/kg to an acidic or neutral pH (for example pH 6.00) with $H_3PO_4$.

2) Heating the mixture to 75° C. with vigorous stirring, and maintaining the mixture at the above temperature for a period of less than 45 minutes, namely 30 minutes.

The temperature is then decreased to 60° C. and the pH is adjusted to 7.5 with a solution of calcium hydroxide.

The method then comprises the stages described for the procedure for plasma proteins, namely enzymatic hydrolysis, separation and purification of the di- and tripeptide-rich hydrolysate and drying.

The molecular distribution of the mixture is identical to that relating to the hydrolysis product of calcium caseinates (Table 3).

V. MILK SERUM SUPPLEMENTED WITH LACTOSE

The problems of antigenicity encountered in specialist nutrition in infants allergic to milk proteins of bovine origin are real.

Currently, it is possible to overcome this problem by subjecting the milk proteins to a hydrolysis method leading to the disappearance of the allergenic property. However, during the addition, to the protein hydrolysate, of a food lactose supplement representing the carbohydrate fraction of the nutriment, contamination of the food by residual proteins occurs (this in spite of the lactose purification stage by crystallisation). These residual proteins then confer an allergenic property on the food.

Enzymatic hydrolysis of milk serum proteins in a medium highly enriched with lactose according to the method of the invention will make it possible to produce a peptide hydrolysate-lactose mixture which can be directly used in infant nutrition.

The operating conditions for the conditioning of the enzymatic hydrolysis and subsequent treatments are identical to those described for milk serum and give similar results.

For example, the level of lactose added to the milk serum can be as high as 300% by weight relative to the weight of the milk serum.

We claim:

1. Method for preparing a di- and tripeptide-rich enzymatic hydrolysate from a protein mixture, in the presence of a proteolytic enzyme, comprising the following steps:

the starting protein mixture is prepared by heat treatment with a temperature between 70° C. and 100° C. at atmospheric pressure at a pH between 4.0 and 8.0 during a period of time between 30 and 45 minutes;

the mixture is subjected to enzymatic hydrolysis with the help of one sole enzyme, added in a ratio of 1 to 4% by weight in regard to the protein which corresponds to 24 to 96 International Units (I.U.) per gram of substrate or 0.024 to 0.096 Anson-unit per gram of substrate, in such a manner that a hydrolysate containing not less than 75 mol. % of di- and tripeptides is obtained with a hydrolyse yield of at least 70 weight-% in regard to the protein mixture; and the hydrolysate is extracted by liquid/solid separation, and then the partially hydrolysed soluble proteins as well as the macropeptides with a molecular mass of more than 10,000 are removed therefrom by ultrafiltration, without affecting the net di- and tri-peptides yield of the product.

2. Method according to claim 1, wherein the protein mixture prepared by heat treatment in order to increase the rate of proteolysis, is hydrolysed at pH values between 6.5 and 9 at temperatures of between 30° and 70° C. for 5 to 9 hours.

3. Method according to claim 1 or 2, wherein the enzyme used for the hydrolysis is a protease which can be used in an alkaline medium.

4. Method according to claim 3, wherein the protease is a serine-containing alkaline protease.

5. Method according to claim 1, wherein the destruction of the enzyme is carried out, when the hydrolysis reaction is considered to be complete, by reducing the pH to between 5.5 and 6.5 by the addition of a strong food acid, selected from a group consisting of HCl, $H_2SO_4$ and $H_3PO_4$, at a temperature of between 70° and 80° C., for 5 to 45 minutes.

6. Method according to claim 1, wherein the protein mixture produced by heat treatment is filtered on a plate and frame filter press in order to remove the free amino acids and other low molecular weight molecules of nonprotein nature and obtain a final di- and tripeptide mixture having a low free amino acid content and low ionic strength.

7. Method according to claim 1, wherein blood plasma is subjected, after adjusting to acidic pH, to a heat treatment in a temperature range between 70° and 100° C. for a period between 30 and 40 minutes, and then to liquid/solid separation by tangential microfiltration or by centrifugation, or by filtration under pressure or vacuum in order to obtain a solid substrate which can be subjected to hydrolysis in the presence of proteolytic enzymes after resuspension.

8. Method according to claim 7, wherein the blood plasma subjected to heat treatment is prepared by adding less than 4 g/l of anticoagulant to the slaughtering blood and then by subjecting the said blood to centrifugation in order to obtain a product which is used immediately or which is suitable for preservation by freezing or drying by spray-drying.

9. Method according to claim 1, wherein a raw material consisting of milk serum proteins is subjected to a prior heat treatment after adjusting the pH to 4.0–5.0, at a temperature of 85° to 100° C., for a period between 30 and 45 minutes, in order to obtain a protein suspension which is then subjected to hydrolysis in the presence of a proteolytic enzyme.

10. Method according to claim 9, wherein food lactose is added to the milk serum proteins before the prior heat treatment.

11. Method according to claim 1, wherein a raw material consisting of proteins chosen from soybean, pea, wheat or fish isolate proteins is subjected to a heat treatment after adjusting the pH to 4–5 at a temperature of 70° to 100° C. for a period between 30 and 45 minutes, in order to obtain a protein suspension which is then subjected to hydrolysis in the presence of a proteolytic enzyme.

12. Method according to claim 1, wherein caseinate is subjected, at pH 6 to 8 to a heat treatment, at a temperature of 70° to 100° C. for a period between 30 and 45 minutes.

13. Method according to claim 1, wherein egg white proteins adjusted to pH 6.0 are subjected to a heat treatment at a temperature of 70° C. for a period between 30 and 40 minutes.

14. Hydrolysate containing di- and tri-peptides obtained by the method of claim 1 from animal and/or vegetable proteins, wherein it is provided in the form of a pulverulent mass of mild savoir and pleasant taste, containing:
   not less than 75 mol. % of di- and tri-peptides;
   less than 5 mol. % of amino acids;
   less than 20 mol. % of peptides of more than three amino acids, the mean chain length being equal to about 6.2.

* * * * *